United States Patent [19]
Maki et al.

[11] Patent Number: 5,476,947
[45] Date of Patent: Dec. 19, 1995

[54] BENZIMIDAZOLE DERIVATIVE AND COMPOSITION FOR TREATING COPPER AND COPPER ALLOY SURFACES COMPRISING THE SAME

[75] Inventors: Yoshiro Maki, Kyoto; Yoshiaki Furukawa, Osaka; Maki Yamanami, Higashiosaka, all of Japan

[73] Assignee: MEC Co., Ltd., Hyogo, Japan

[21] Appl. No.: 250,350

[22] Filed: May 26, 1994

Related U.S. Application Data

[63] Continuation of Ser. No. 994,318, Dec. 21, 1992, abandoned.

[30] Foreign Application Priority Data

Jan. 8, 1992 [JP] Japan .................................. 4-018415

[51] Int. Cl.$^6$ ................................................ C07D 235/08
[52] U.S. Cl. ..................................... 548/304.4; 548/310.4
[58] Field of Search ............................... 548/304.4, 310.4

[56] References Cited

U.S. PATENT DOCUMENTS

| | | | |
|---|---|---|---|
| 3,325,506 | 6/1967 | Jones et al. | 548/304.4 |
| 3,897,439 | 7/1975 | Frey | 548/304.4 |
| 4,074,046 | 2/1978 | Mohan | 548/304.4 |

FOREIGN PATENT DOCUMENTS

| | | |
|---|---|---|
| 0428260 | 5/1991 | European Pat. Off. . |
| 0513831 | 11/1992 | European Pat. Off. . |
| 3540376 | 5/1987 | Germany . |
| 3-76753 | 4/1991 | Japan . |
| 89212157 | 4/1991 | Japan . |
| 3-124395 | 5/1991 | Japan . |
| 849793 | 9/1960 | United Kingdom ................ 548/304.4 |

OTHER PUBLICATIONS

Murray et al, "Inhibition of rat hepatic, etc" *J. Med Chem* (1982) 25(8) pp. 887–892.
Galust'yan, "Syntheis of substituted, etc" CA 91: 140777n (1978).
Dandegaonker et al I, "Bromobenzimidazoles" CA 63: 4274a (1965).
Dandegaonker et al II, "4(7) Halobenzimidazoles" CA 59: 10023d (1963).
Chaudhury et al, "Syntheses of condensed, etc" CA 97: 722942 (1982).
Popov et al, "Preparation of (2–substituted), etc" CA 115: 8804d (1991).
Paglietti et al, "Preparation and pharmacological, etc" CA 109: 66339t (1988).
Ozden et al, "Studies on the structure–activity, etc" CA 110:20983r (1989).
Kondo et al, "Ruthenium complex–catalyzed, etc" CA 115:92159c (1991).
Elderfield et al, "The reaction of o–phenylenediamines, etc" CA 54: 16447f (1960).
Fokken et al, "Preparation of compounds With, etc" CA 88: 190708z (1978).
Gumus et al, "Synthesis and in vitro antibacterial, etc" CA 110: 132041p (1989).
English language abstract for 3–124395, May 27, 1991.
Abstract of Japanese JP–A–89 258564 (Hideyui Kawai) May 27, 1991.
Translation, pp. 6 and 7, and Formulae I and II of Japanese–A–89 258264 May 27, 1991.
Chem. Abs. 115–115831g (Japanese–A–89 212157) Apr. 2, 1991.

Primary Examiner—Patricia L. Morris
Attorney, Agent, or Firm—Oliff & Berridge

[57] ABSTRACT

A novel benzimidazole derivative is disclosed. The benzimidazole derivative is represented by the following formula (I),

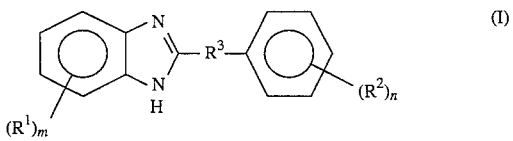

wherein $R^1$ is a hydrogen atom, a lower alkyl group, or a halogen atom; $R^2$ is a hydrogen atom or a lower alkyl group; $R^3$ is an alkylene group with 1 to 18 carbon atoms; and n and m are integers from 0 to 3. The compound has an excellent rust preventing effect and can be used as a component of a composition for the treatment of surfaces of copper and copper alloys comprising the benzimidazole derivative which is particularly useful in preventing rust in printed-wiring boards.

2 Claims, 3 Drawing Sheets

BENZIMIDAZOLE DERIVATIVE AND COMPOSITION FOR TREATING COPPER AND COPPER ALLOY SURFACES COMPRISING THE SAME

This is a continuation of application Ser. No. 07/994,318 filed Dec. 21, 1992, now abandoned.

BACKGROUND OF THE INVENTION

1. Field of the Invention

The present invention relates to a benzimidazole derivative having a rust preventing effect and to a composition for the treatment of surfaces of copper and copper alloys comprising the benzimidazole derivative which is particularly useful in preventing rust in printed-wiring boards.

2. Description of the Background Art

Methods for prevention of rust in a circuit formed from copper or a copper alloy on a printed-wiring board and for maintaining the adherence of solder include a method of covering the circuit with another metal, for example, a method of plating with solder, gold, palladium, or the like, a method of coating with solder by the so-called hot air leveler method, and a method of covering with an organic film.

Examples of materials which form the organic film used in the last-mentioned method include a rosin-type preflux, which coats the entire printed-wiring board, and an alkylimidazole-type preflux which forms a film by a chemical reaction selectively on the copper circuit section.

The rosin-type preflux is used in a method for forming a film by coating, spraying, or soaking the entire printed-wiring board with a solution of a natural rosin, a rosin ester, a rosin-modified maleic acid resin, or the like, in an organic solvent, and then drying. However, this method involves a problem of impairing the working environment and the safety because of volatilization of the organic solvent.

The alkylimidazole-type preflux is soluble in water and is superior from the aspect of keeping a good working environment and safety. The compound, however, deteriorates when subjected to a high temperature, hindering the action of a postflux which is used during soldering and thus giving a rise to the drawback of poor solder adherence.

In recent years, a surface mounting method has become the most commonly used method for joining electronic parts on a printed-wiring board. This increases opportunities wherein printed-wiring boards are exposed to high temperatures, e.g., temporary mounting of the parts, reflow of creamy solders, and the like. For this reason, a treatment agent which does not lower the adherence of the solder, even when the printed-wiring boards have been exposed to high temperatures, is required.

An invention responding to such a requirement is disclosed in Japanese Patent Laid-open (ko-kai) No. 124395/1991, which provides a preflux using a benzimidazole derivative with a hydrogen atom, an alkyl group, or an aryl group in 2-position of the imidazole ring.

Although the benzimidazole derivatives can satisfy the above-mentioned heat resistance requirement to a certain degree, they cannot be a breakthrough for the ever increasing requirements more stringently imposed on the adherence of the solder after exposure to a high temperature.

In view of this situation, the present inventors have synthesized a number of compounds and studied their applicability as a preflux and their heat resistance. As a result, the present inventors have found that certain novel benzimidazole derivatives can produce superior films on the surfaces of copper or copper alloys, which can be excellently soldered without using a volatile solvent even after the surfaces have been exposed to a high temperature.

SUMMARY OF THE INVENTION

Accordingly, an object of the present invention is to provide a benzimidazole derivative represented by the following formula (I),

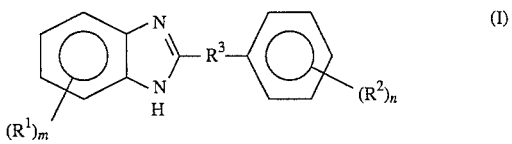

wherein $R^1$ is a hydrogen atom, a lower alkyl group, or a halogen atom; $R^2$ is a hydrogen atom or a lower alkyl group; $R^3$ is an alkylene group with 1 to 18 carbon atoms; and n and m are integers from 0 to 3.

Another object of the present invention is to provide a composition for treating a surface of copper or a copper alloy comprising said benzimidazole derivative as an effective component.

These and other objects, features, and advantages of the present invention will become more apparent from the following description of the preferred embodiments taken in conjunction with the accompanying drawings.

DETAILED DESCRIPTION OF THE INVENTION AND PREFERRED EMBODIMENTS

Figure 1:
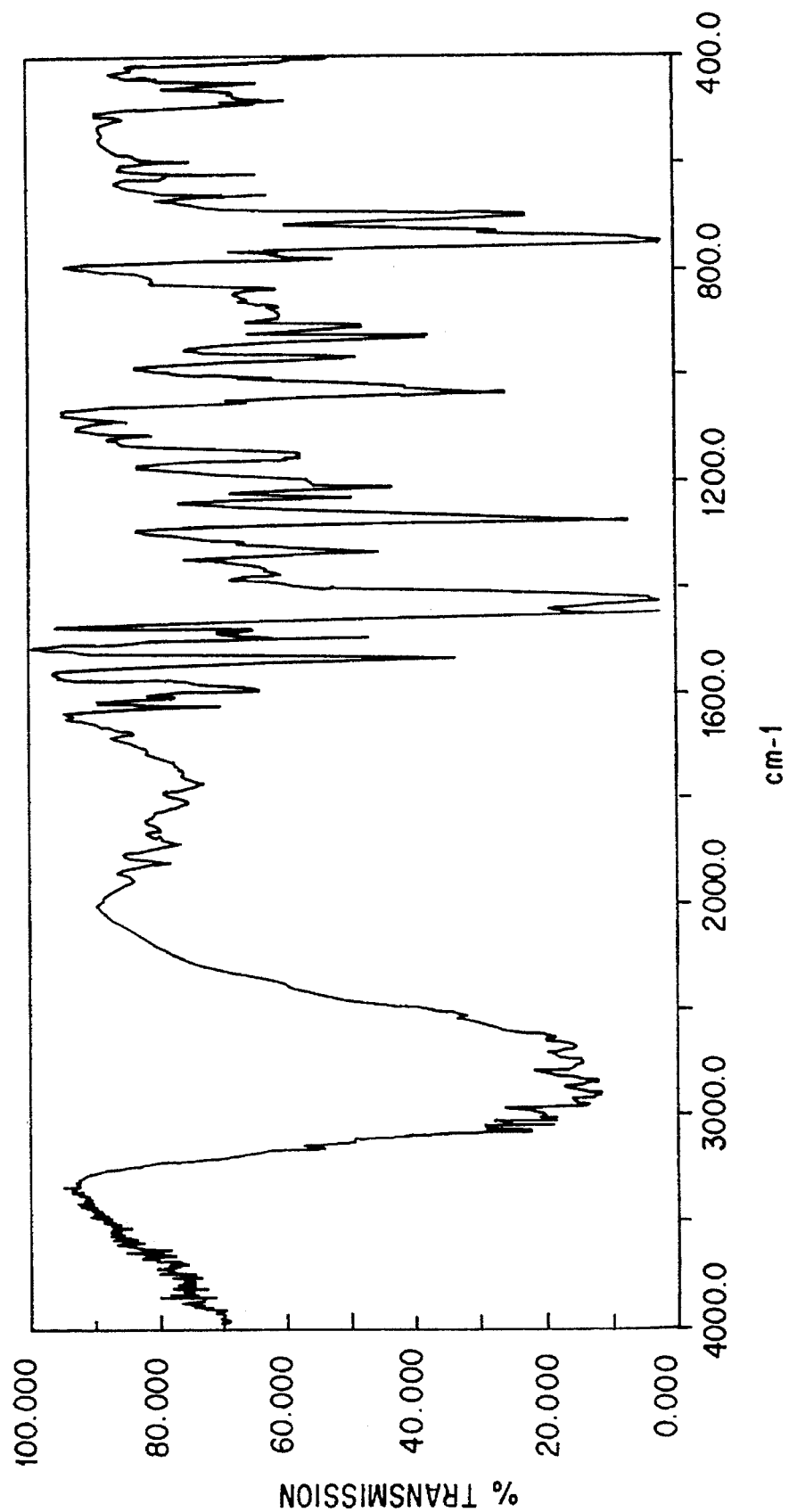
FIG. 1 is an FT-IR spectrum of Compound 1 of the present invention prepared in Example 1.

In formula (1) representing the benzimidazole derivatives if the present invention, $R^1$ is a hydrogen atom, a lower alkyl group having 1 to 4 carbon atoms, such as, for example, methyl group, ethyl group, n-propyl group, isopropyl group, n-butyl group, tert-butyl group, or the like, or a halogen atom such as Cl, Br, or the like. $R^2$ is a hydrogen atom or a lower alkyl group having 1 to 4 carbon atoms, such as, for example, methyl group, ethyl group, n-propyl group, n-butyl group, or nonyl group, or the like. $R^3$ is an alkylene group having 1 to 18, and preferably 2 to 8 carbon atoms, such as, for example, methyl, ethyl, propyl, butyl, octyl, nonyl or undecyl group, or the like. These alkylene groups may also be branched. They may also have an unsaturated bond or other substituted group.

Compounds in which the imidazole is directly bonded to the phenyl or aralkyl group without an $R^3$ group in formula (1) does not form a film on a copper or a copper alloy surface required for soldering and other processing. On the other hand, compounds having an alkylene group for $R^3$ in formula (1) having carbon atoms exceeding 18 are technically difficult to produce. In addition, their solubility is insufficient and the process is uneconomical.

Given as specific examples of the compounds of formula (1), which can be preferably used as the active ingredient of the composition of surface treatment agent for copper and copper alloys, are 2-(phenylalkyl)benzimidazoles such as, 2-benzylbenzimidazole,
2-(2-phenylethyl)benzimidazole,
2-(3-phenylpropyl)benzimidazole,
2-(2-phenylpropyl)benzimidazole,
2-(4-phenylbutyl)benzimidazole,
2-(3-phenylbutyl)benzimidazole,
2-(9-phenylnonyl)benzimidazole,
2-(8-phenyloctyl)benzimidazole,
2-(11-phenylundecyl)benzimidazole,
2-(10-phenylundecyl)benzimidazole, and the like;

2-(phenylalkyl)alkylbenzimidazoles such as, 2-benzyl-5-methylbenzimidazole,
2-benzyl-5-ethylbenzimidazole,
2-(2-phenylethyl)-5-methylbenzimidazole,
2-(2-phenylethyl)-5-ethylbenzimidazole,
2-(3-phenylpropyl)-4-ethylbenzimidazole,
2-(2-phenylpropyl)-5-methylbenzimidazole,
2-(4-phenylbutyl)-5-methylbenzimidazole,
2-(3-phenylbutyl)-4-ethylbenzimidazole, and the like;

2-(alkylphenylalkyl)alkylbenzimidazoles such as, 2-(2-tolylethyl)-5-methylbenzimidazole,
2-(3-tolylpropyl)-4-ethylbenzimidazole,
2-(2-tolylpropyl)-5-methylbenzimidazole,
2-(2-xylylethyl)-5-methylbenzimidazole,
2-(3-xylylpropyl)-4-methylbenzimidazole,
2-(2-xylylpropyl)-5-ethylbenzimidazole, and the like.

The benzimidazole derivative of the present invention, for example 2-(phenylalkyl)benzimidazole, can be easily prepared by reacting a higher fatty acid containing a phenyl group which becomes a part of the two-position substituted group of the compound and o-phenylenediamine while heating at 170° to 200° C. using p-toluene sulfonic acid as a medium, and then removing the unreacted fatty acid and the like. The resulting compound can be confirmed by the FT-IR spectrum, UV spectrum, and the like.

There are no particular limitations on the utilization of the benzimidazole derivative of the present invention. It is, for example, useful as a curing agent for epoxy resins, a dying adjuvant, an intermediate for the production of an organic synthetic compound, and the like, in addition to its use as a composition for a surface treatment agent for copper and copper alloys as described in detail in the following.

In order to solubilize or emulsify the benzimidazole derivative of the present invention when used as a composition for the surface treatment of copper and copper alloys, the compound is usually mixed with an aqueous solution containing an organic acid such as formic acid, acetic acid, propionic acid, glycolic acid, n-butyric acid, isobutyric acid, acrylic acid, crotonic acid, isocrotonic acid, oxalic acid, malonic acid, succinic acid, adipic acid, maleic acid, acetylene dicarboxylic acid, monochloroacetic acid, trichloroacetic acid, lactic acid, oxybutyric acid, glyceric acid, tartaric acid, malic acid, citric acid, or the like; an inorganic acid such as hydrochloric acid, sulfuric acid, nitric acid, phosphoric acid, or the like; or a metal compound such as zinc acetate, zinc sulfate, zinc phosphate, zinc chloride, lead acetate, iron oxide, copper chloride, copper phosphate, copper carbonate, copper acetate, or the like; or with an aqueous solvent such as methanol, ethanol, isopropyl alcohol, ethyleneglycol monomethyl ether, ethyleneglycol monoethyl ether, or the like.

The above organic acids, inorganic acids, metal compounds, and aqueous solvents can be used individually or two or more of them can be used mixed in any optional ratio for solubilizing or emulsifying the benzimidazole derivative. In addition, various additives conventionally used in surface treatment agents may be added as required.

The amount of the benzimidazole derivative of the present invention used in the composition for surface treatment is preferably 0.1% to 5.0% by weight.

The composition of the present invention may be applied to the surface of the copper or copper alloy for the treatment of the surface by using a method such as soaking, spraying, application with a roller coater, or painting with a paint brush.

Other features of the invention will become apparent in the course of the following description of the exemplary embodiments which are given for illustration of the invention and are not intended to be limiting thereof.

EXAMPLES

Example 1

<Preparation of 2-(5-phenylpentyl)benzimidazole>

108 gm (1 mol) of o-phenylenediamine, 192 gm (1 mol) of 6-phenylhexanoic acid, and 190 gm (1 mol) of p-toluene sulfonic acid monohydrate were thoroughly blended and heated using a mantle heater under agitation. The temperature was raised to 200° C. in 30 to 40 minutes, then the mixture was heated at 200° to 220° C. for 3 to 4 hours until evaporation of steam has almost terminated. The balance of the liquid was driven off at close to 160° to 170° C., the material was melted, and then liquefied. After the heating was completed, the reaction mixture was poured into aqueous ammonia, agitated, and the solidified material was filtered, washed with water, and dried to provide a blue-purple powder.

Figure 2:
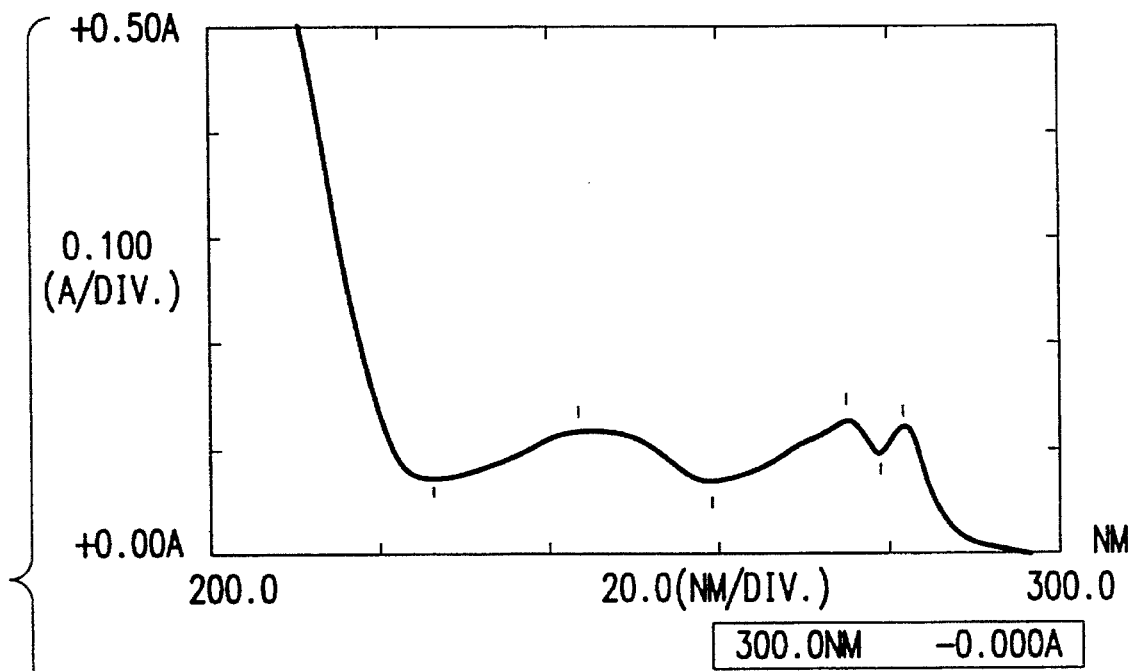
FIG. 2 is a UV absorption spectrum of Compound 1.
Figure 3:
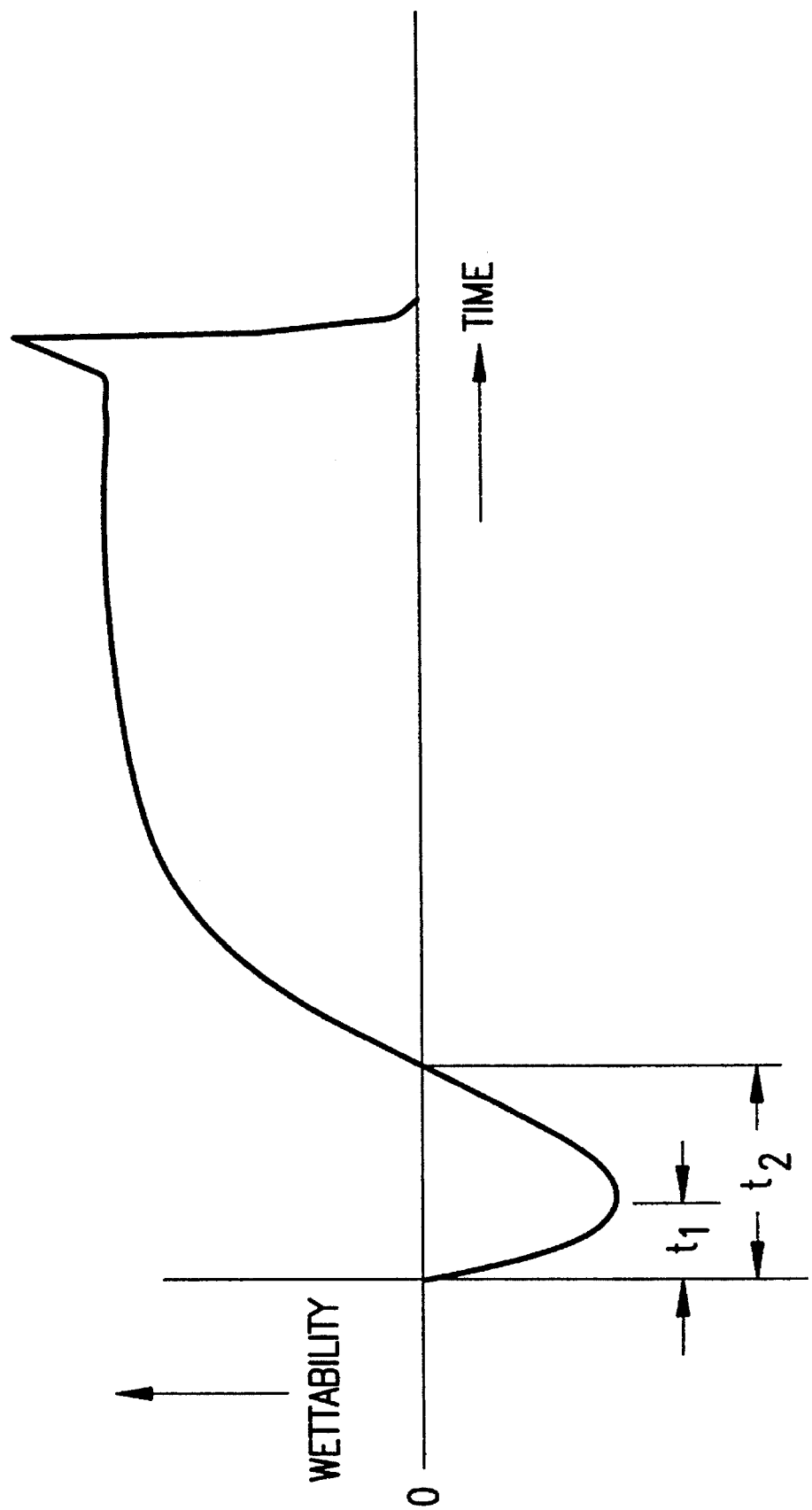
FIG. 3 is a wettability curve for the determination of the soldering wettability by the Meniscograph method, wherein $t_1$ indicates the time from start of immersion until a peak of buoyancy from surface tension is reached, which is determined from the rate of immersion and the time at which wetting commences, and $t_2$ is the time from start of immersion until buoyancy from surface tension becomes zero, i.e. the time when the contact angle reaches 90°.

The resulting powder was recrystallized with a solvent to obtain white, needle-shaped crystals of 2-(5-phenylpentyl)benzylbenzimidazole (Compound 1) of the present invention at an yield of greater than 90%. The compound had a melting point of 136°–138° C. The FT-IR and UV absorbance of this compound were measured with the results shown in FIG. 1 and FIG. 2, to confirm that the target compound was obtained.

Examples 2 to 11

<Preparation of various benzimidazole derivatives>

The benzimidazole derivatives (Compounds 2–11 of the present invention) listed in Table 1 were synthesized in the same manner as in Example 1.

Example 12

<Composition for copper or copper alloy surface treatment>

An aqueous solution of each benzimidazole derivative (1 g) prepared in Examples 2–11 dissolved in acetic acid to saturate the acetic acid were prepared. Another solution was prepared by adding 0.04 g of cuprous chloride to 0.1 g of 25% aqueous ammonia and thoroughly stirring the mixture. Each solution, i.e. the benzimidazole derivative solution and the cuprous chloride solution were added to 100 g of water, followed by stirring, thus obtaining a treating solution.

A number of 1 cm×5 cm×0.3 mm copper test specimens were prepared by a surface cleaning process comprising defatting, washing with water, microetching [a procedure of dipping the test specimen in Mec Bright CB-801 (a solution containing sulfuric acid and hydrogen peroxide, trade mark a product of Mec Co.) for 1 minute at room temperature], and washing with water. Each test specimen was immersed in one of the above-mentioned solutions for one minute at 40° C., washed with water, and dried, then heated in a hot air circulation apparatus for 10 minutes at 200° C. A postflux was applied to each of these test specimens and a wettability test was carried out by the surface tension method (Meniscograph method). The results of these tests are given in Table 1.

Comparative Example 1

One gram of 2-undecyl-4-imidazole (Comparative Compound 1) was added to 2 gm of acetic acid and mixed to prepare a homogeneous solution. Separately, 0.04 gm of cuprous chloride was added to 0.6 gm of a 25% aqueous ammonia solution and stirred thoroughly to make a solution. The both solutions were respectively added to 100 gm of water and mixed thoroughly to prepare a treating liquid.

A 1 cm×5 cm×0.3 mm test specimen was prepared by the surface cleaning process comprising defatting, washing with water, microetching (Mec Bright CB-801, Mec Co.), and washing with water. This test specimen was immersed in the above-mentioned 2-undecyl-4-imidazole solution for one minute at 30° C., washed with water, and dried, then heated in a hot air circulation apparatus for 10 minutes at 200° C. A postflux was applied to this test specimen and a wettability test was carried out in the same manner as in the Example 12.

The results are shown in Table 1 together with the results obtained in Example 12.

Comparative Example 2

One gram of 2-methylbenzimidazole (Comparative Compound 2) was added to 2 gm of acetic acid and mixed to prepare a homogeneous solution. Then, 100 gm of water was slowly added to the solution, followed by the addition of 0.02 gm of cupric chloride. The mixture was thoroughly stirred to prepare a treating liquid.

A 1 cm×5 cm×0.3 mm test specimen was prepared by the surface cleaning process comprising defatting, washing with water, microetching (Mec Bright CB-801, Mec Co.), and washing with water. This test specimen was immersed in the 2-methylbenzimidazole solution for one minute at 40° C., washed with water and dried, then heated in a hot air circulation apparatus for 10 minutes at 200° C. A postflux was applied to this test specimen and a wettability test was carried out in the same manner as in the Example 12.

The results are shown in Table 1.

Comparative Example 3

One gram of 2-phenyl-5-methylbenzimidazole (Comparative Compound 3), 20 gm of acetic acid, and 1 gm of methanol were homogeneously blended. Then, 100 gm of water was slowly added to the solution, followed by the addition of 0.02 gm of cupric chloride. The mixture was thoroughly stirred to prepare a treating liquid.

A 1 cm×5 cm×0.3 mm test specimen was prepared by the surface cleaning process comprising defatting, washing with water, microetching (Mec Bright CB-801, Mec Co.), and washing with water. This test specimen was immersed in the 2-phenyl-5-methylbenzimidazole solution for one minute at 40° C., washed with water and dried, then heated in a hot air circulation apparatus for 10 minutes at 200° C. A postflux was applied to this test specimen and a wettability test was carried out in the same manner as in the Example 12.

The results are shown in Table 1.

TABLE 1

| | Benzimidazole Derivative | Soldering Wettability (sec) | |
|---|---|---|---|
| | | $t_1$ | $t_2$ |
| Compound | | | |
| 1 | 2-(5-phenylpentyl)benzimidazole | 0.49 | 1.23 |
| 2 | 2-benzylbenzimidazole | 0.49 | 1.12 |
| 3 | 2-(2-phenylethyl)benzimidazole | 0.43 | 1.10 |
| 4 | 2-(3-phenylpropyl)benzimidazole | 0.46 | 1.27 |
| 5 | 2-(4-phenylbutyl)benzimidazole | 0.48 | 1.21 |
| 6 | 2-(9-phenylnonyl)benzimidazole | 0.51 | 1.30 |
| 7 | 2-benzyl-5-methylbenzimidazole | 0.47 | 1.42 |
| 8 | 2-benzyl-5-ethylbenzimidazole | 0.49 | 1.38 |
| 9 | 2-(2-phenylethyl)-5-methylbenzimidazole | 0.45 | 1.26 |
| 10 | 2-(4-phenylbutyl)-5-methylbenzimidazole | 0.47 | 1.23 |
| 11 | 2-(2-tolylethyl)-5-methylbenzimidazole | 0.53 | 1.40 |
| Comparative Compound | | | |
| 1 | 2-undecyl-4-imidazole | Not wettable | |
| 2 | 2-methylbenzimidazole | Not wettable | |
| 3 | 2-phenyl-5-methylbenzimidazole | 0.73 | 3.37 |

The present invention provides novel benzimidazole derivatives. The benzimidazole derivatives are suitable as a composition for surface treatment of copper and copper alloys. The composition for the surface treatment of the present invention has superior heat resistance and provide a film with extremely good adherence of solder on the surface of the copper or copper alloy even after exposure to high temperatures. Thus, the composition exhibits a particularly remarkable effect when electronic parts are mounted on the surface of a printed-wiring board.

Obviously, numerous modifications and variations of the present invention are possible in light of the above teachings. It is therefore to be understood that within the scope of the appended claims, the invention may be practiced otherwise than as specifically described herein.

What is claimed is:

1. A benzimidazole derivative represented by the following formula (I),

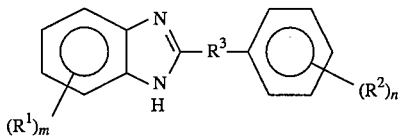

wherein $R^1$ is a hydrogen atom, a lower alkyl group, or a halogen atom; $R^2$ is a hydrogen atom or a lower alkyl group; $R^3$ is an alkylene group with 5–9 carbon atoms; and n and m are integers from 0 to 3, with the proviso that n=0 when $R^3$ is an alkylene group with 9 carbon atoms.

2. A benzimidazole derivative according to claim 1, selected from the group consisting of 2-(5-phenylpentyl)benzimidazole, 2-(9-phenylnonyl)benzimidazole, 2-(8-phenyloctyl)benzimidazole, and 2-(2-tolylethyl)-5-methylbenzimidazole.

* * * * *